United States Patent [19]
Pollack et al.

[11] Patent Number: 5,666,104
[45] Date of Patent: Sep. 9, 1997

[54] BELT FOR DETECTING AN INCREASE IN GIRTH

[76] Inventors: Stanley E. Pollack, 32100 Gates Mills Blvd., Pepper Pike, Ohio 44124; Scott C. Marlow, 12441 Bentbrook Dr., Chesterland, Ohio 44026; Haans K. Petruschke, 9103 Chillicothe Rd. #103, Kirtland, Ohio 44094

[21] Appl. No.: 525,910

[22] Filed: Sep. 7, 1995

[51] Int. Cl.⁶ ................................................. G08B 23/00
[52] U.S. Cl. ........................................... 340/573; 128/780
[58] Field of Search ........................... 340/573, 574, 340/665, 529, 407.1; 128/780, 96.1; 119/51.02

[56] References Cited

U.S. PATENT DOCUMENTS

| | | | |
|---|---|---|---|
| 2,671,899 | 3/1954 | Kroger | 128/96.1 X |
| 3,670,320 | 6/1972 | Palmer | 340/573 |
| 4,191,949 | 3/1980 | Myers | 340/573 |
| 4,300,129 | 11/1981 | Cataldo | 340/573 X |
| 4,392,126 | 7/1983 | Loyola | 340/573 |
| 4,559,953 | 12/1985 | Wright et al. | 128/680 |
| 4,592,342 | 6/1986 | Salmasian | 128/898 |
| 4,807,640 | 2/1989 | Watson et al. | 128/721 |
| 4,817,625 | 4/1989 | Miles | 128/721 |
| 4,823,808 | 4/1989 | Clegg et al. | 128/773 |
| 4,871,998 | 10/1989 | Chaillou | 340/573 |
| 5,207,230 | 5/1993 | Bowers | 128/780 |
| 5,263,491 | 11/1993 | Thornton | 128/774 |
| 5,304,984 | 4/1994 | Roldan | 340/573 |
| 5,398,688 | 3/1995 | Laniado | 128/660.02 |

FOREIGN PATENT DOCUMENTS

| | | | |
|---|---|---|---|
| 261096 | 9/1961 | Australia | 340/573 |
| 2539983 | 8/1984 | France | 340/573 |
| 2245737 | 1/1992 | United Kingdom | 340/573 |

*Primary Examiner*—Thomas Mullen
*Attorney, Agent, or Firm*—Thompson Hine & Flory LLP

[57] ABSTRACT

A device for monitoring the volume of food consumed during a meal includes a sensor and a belt. The sensor includes a sensor housing, an alarm, and an activation switch operatively connected to the alarm; and the belt is adapted to be worn about the waist of a user, and is operatively connected to the sensor, such that a predetermined tensile force applied to the belt, caused by the consumption of food by the user, activates the switch, and in turn, activates the alarm. Preferably, the sensor includes a delay circuit connected between the activation switch and the alarm such that the tensile force must be applied continuously for a desired time interval before the alarm is activated.

23 Claims, 2 Drawing Sheets

BELT FOR DETECTING AN INCREASE IN GIRTH

BACKGROUND

The present invention relates to devices for helping to prevent excessive eating and, more particularly, to devices which emit an alarm in response to the increase in the girth of an individual beyond a predetermined limit due to excessive consumption of food.

Obesity has become one of the most pervasive health problems in the United States, affecting over 60 million individuals. Some studies claim that 35% of women, 31% of men, and 25% of children in the United States are considered clinically obese.

An overweight individual may desire weight loss for appearances, but the disease has more serious and far reaching consequences that may lead to life threatening diseases. The health care community has linked to obesity increased risks of high blood pressure leading to hypertension, high levels of blood glucose associated with diabetes, high concentrations of blood cholesterol and triglycerides which are associated with the cardiovascular disease, certain types of cancer, increased stress on weight-bearing joints leading to arthritis, depression, sleep apnea and gall bladder disease.

Treatment of obese individuals varies widely from self designed diets to professional programs utilizing very low calorie diets, psychological counseling and weekly monitoring. Tens of millions of Americans at any given time are involved in some type of diet plan. Generally, however, many current dieting methods fail. It is believed that high incidence in failed programs results in progressive weight gain. Many believe that solutions to obesity depend on a long term approach of gradual, yet continuous weight loss until desired body weight goals are obtained. These solutions typically include a combination of diet and exercise. In addition to eating the "right" kinds of foods (e.g., low fat foods), weight loss can be effected by reducing the volume of food ingested at each meal.

Accordingly, there is a need for a device which monitors the volume or mass of food consumed at a meal, and which signals that individual when a predetermined amount of food has been consumed.

SUMMARY OF THE INVENTION

The present invention is a belt, worn around the abdomen of a subject at the umbilicus level, which detects the expansion of the patient's girth at that level in response to food consumption. Once the device detects that the girth has expanded to a predetermined limit, the device will emit an alarm, signalling to the subject that an adequate amount of food has been consumed.

In accordance with the present invention, a device for monitoring an individual's girth during the individual's consumption of food comprises a sensor having an alarm, and first and second belt segments joined by an adjustable buckle. The free ends of the belt segments are joined together by the buckle. The sensor is mounted within a housing and to the first belt segment to detect displacement of that belt segment away from the sensor housing. The alarm of the sensor emits a signal in response to such detection and can be triggered after a delay, so that the alarm is not triggered by a temporary increase in girth resulting from breathing, coughing or sneezing. In a preferred embodiment, the alarm is a vibrating device whose operation can be detected only by the wearer.

Preferably, a spring is connected between the sensor housing and the second belt segment such that a particular amount of force is required to displace the belt segment in a direction away from the housing. Also, the sensor includes a three-position switch which, in one position provides power to sensor and delay circuits, in a second position cuts power to sensor and delay circuits, thereby shutting down the device, and in a third position provides power to the sensor circuit while disabling the delay circuit. Therefore, in the first position the sensor (and hence the belt) will be active (ON MODE), in the second position the sensor will be powered down (OFF MODE) and in the third position the sensor is active but bypasses the delay circuit (SET-UP/TEST MODE).

Accordingly, it is an object of the present invention is to provide a device and method in which a user can discretely monitor the volume of food intake; a device which monitors the volume of food intake which is reliable in operation; and a monitoring device which is relatively easy to use and relatively inexpensive to manufacture.

Other objects and advantages of the present invention will be apparent from the following description, the accompanying drawings and the appended claims.

DETAILED DESCRIPTION

Figure 1:
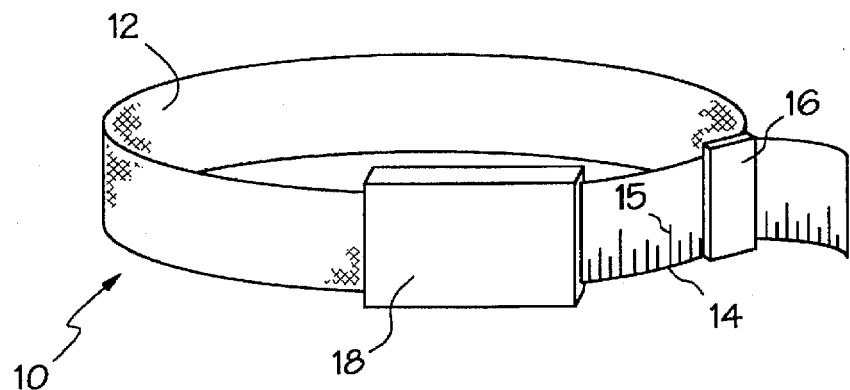
FIG. 1 is a perspective view of a preferred embodiment of the belt for detecting an increase in girth of the present invention.

As shown in FIG. 1, the girth monitoring belt of the present invention, generally designated 10, includes two belt segments 12, 14 which are adjustably connected to each other by a conventional buckle 16. Belt segment 14 is adjustably attached to a sensor housing 18 and belt segment 12 is fixed to the sensor housing. Belt segment 14 has inch and fractional inch graduations 15 printed thereon, although any type of measurement unit or indicator may be printed on the strap instead. Buckle 16 is a military style buckle with a frictional engagement which allows for infinite adjustment of belt 10 circumference and tightness, although any type of belt or strap coupling mechanism may also be used.

It is also within the scope of the invention to have only a single belt segment, with the free ends being adjustably connected to opposite ends of the sensor housing 18 by a buckle engagement or other similar means.

Figure 2:
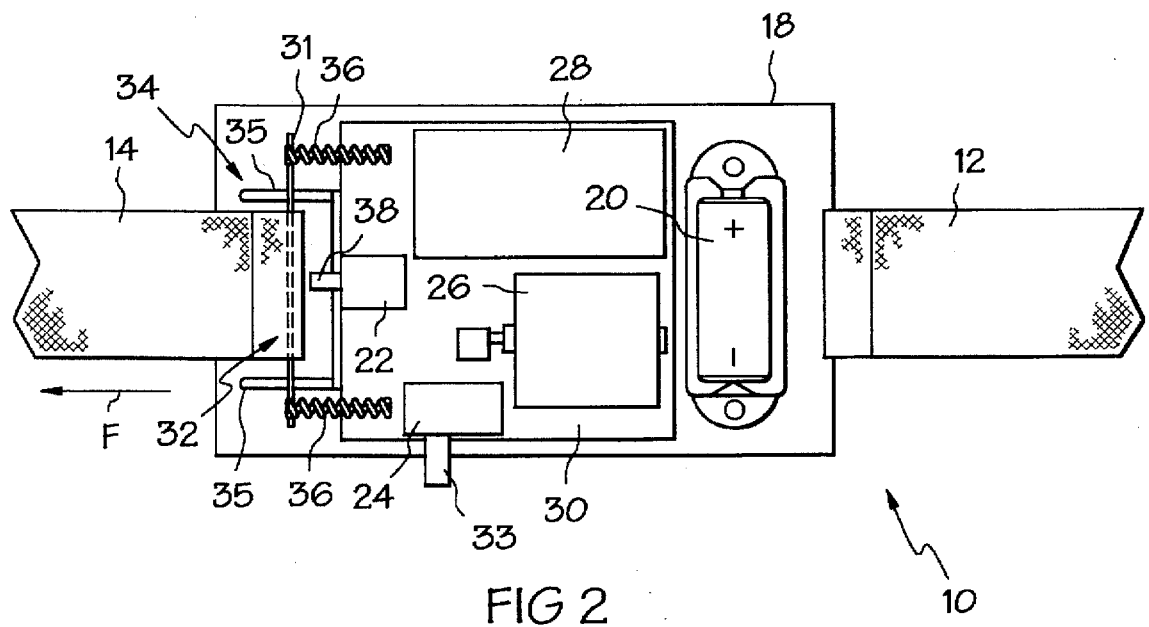
FIG. 2 is a schematic, sectional view of the sensor housing of FIG. 1.

As shown in FIG. 2, the sensor housing 18 includes a battery 20, a conventional spring biased contact switch 22 having spring loaded switch 38 (see also FIG. 3), a three-position switch 24, an alarm circuit 26 and a delay circuit 28. Switch 22, switch 24, alarm circuit 26 and delay circuit 28 comprise the device circuitry 29 (see FIG. 3), and are collectively mounted on a circuit board 30 which, in turn, is mounted within the sensor housing 18. Switch 24 is positioned such that the switch lever 33 projects below the housing 18. Pin 31 extends through a loop sewn into the end 32 of belt segment 14 and slides within the forks 35 of a cradle 34 mounted in the sensor housing 18. A pair of extension springs 36 are attached to and extend between the pin 31 and the circuit board 30 to apply a tensile force to the belt segment 14 to resist movement of the end 32 of belt segment 14 in the direction of arrow F away from the sensor housing. The net force of the springs 36 (i.e., overcoming the spring force of button 38) is preferably between 15 and 25 ounces (4.2N and 7N).

The contact 38 extends through a hole (not shown) in the cradle 34. Therefore, when there is no tensile force, or insufficient tensile force on the belt segment 14 to overcome the compressive forces of springs 36, applied on the belt strap 14 in the direction F away from the sensor housing, loop 32 will be drawn against contact 38 which causes switch 22 to be "open." Switch 22 will "close" when there is a tensile force in the F direction sufficient to displace the loop 32 (and hence pin 31 in cradle 34) away from switch contact 38. Consequently, switch 22 acts to detect when a particular tensile force is applied to the belt 10 which causes end 32 of belt segment 14 to be displaced in the F direction away from or out of the sensor housing 18. When the device is being worn about the waist of a subject, this tensile force will be caused by an increase in the girth of the abdomen of the subject.

It is therefore within the scope of the invention to use any suitable sensor, capable of sensing such a tensile force applied to the end 32 of belt segment 14 in the F direction, in place of contact switch 22. An example of an adequate momentary switch 22 for use with the present invention is Cat. No. UX40E50A01, commercially available from MICRO SWITCH, Freeport, Ill. (a division of Honeywell Inc.). An example of the three-position switch 24 is an ON-NONE-ON slide-switch, such as cat. no. EG2215, commercially available from Electronics Components Group Inc., Minneapolis, Minn. (a.k.a. E-SWITCH). Preferably, one ON position of the switch 24 connects power to the device circuitry 29 and configures the device circuitry to include the delay circuit 28 (ON MODE); the other ON position couples power to the device circuitry 29 but configures the device circuitry to bypass the delay circuit 28 (SET-UP/TEST MODE); and the NONE position essentially decouples power to the device circuitry (OFF MODE). It is also within the scope of the invention to provide two separate switches or switching means in place of the three-position switch: one switch would be used to effectively couple/decouple power to the device circuitry, and the other switch would be used to effectively enable/disable the delay circuit.

Alarm 26 is preferably a low voltage motor with an eccentric weight, which when activated creates a vibration which passes through the housing 18 to the wearer's abdomen. Examples of such a load motor with an eccentric weight include cat. no. RF-410CH-13210 (1.0 to 2.0 V; current, no load 0.031 A, max. eff. 0.107 A @ 1.9 V), cat. no. SU-020SA-09170 (1.0 to 3.0 V; current, no load 0.065 A, max. eff. 0.160 A @ 3 V), or cat. no. SH-030SA-09170 (4.5 to 9.0 V; current, no load 0.090 A, max. eff. 0.225 A @ 6 V), all commercially available from Mabuchi Motor America Corp., New York, N.Y. Therefore, the circuit can be configured for 1.5, 3.0 or 9 volt batteries 20 or other suitable power supplies. Other suitable, and preferably discrete, alarms such as audible alarms may also be used in place of the above listed alarms.

The delay circuit 28, when incorporated in circuit 29, preferably postpones the triggering of the alarm 26 for 5 to 7 seconds. If the switch 22 remains in the "closed" position continuously during this delay, then the alarm will be triggered. The delay circuit 28 is used to delay the activation of the alarm for 5 to 7 seconds to prohibit the normal breathing cycle or extreme motions, such as bending over to pick up an object, from creating "false on" conditions. It is also within the scope of the invention to adjust the delay time so that the device 10 is either more or less sensitive, depending upon the desired operation. An example of an adequate delay circuit 28 for use with the present invention is a conventional delay switch, KH1, commercially available from Instrumentation and Control Systems Inc., Addison, Ill.

Figure 3:
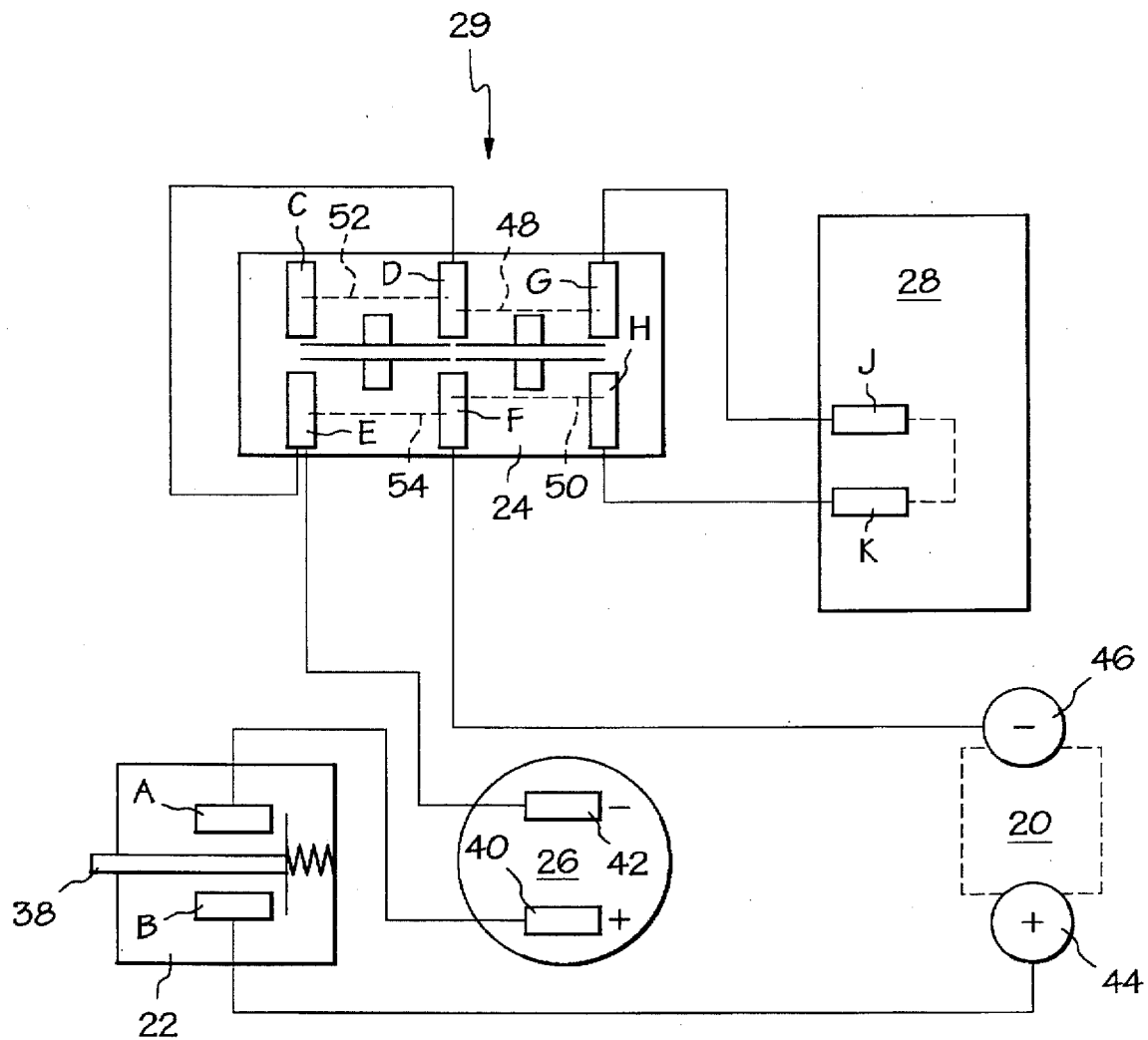
FIG. 3 is a schematic wiring diagram of the preferred embodiment.

As shown in FIG. 3, the alarm 26 will be triggered when a circuit is completed between the positive and negative contacts 40,42 of the alarm and the positive and negative leads 44,46 of the battery 20. The three-position switch 24 is shown in FIG. 3 switched to the NONE position. In this position, the negative lead 46 from the battery 20 cannot be coupled to the negative contact 42 of the alarm 26 so that the alarm cannot be triggered.

When the three-position switch 24 is switched by the user to the first ON position, contact D is connected to contact G, and contact F is connected to contact H as shown by broken lines 48,50. As shown in FIG. 3, contacts G and H of switch 24 are connected to contact J and K of delay circuit 28. Thus, in the first ON position, the negative lead 46 from the battery 20 is connected to the negative contact 42 of the alarm 26 through delay circuit 28. Since current passes from terminal 46, through contacts F, H, and K, through delay circuit 28, then through contacts J, G, D and E to terminal 42. Therefore, when the momentary switch 22 is closed by a sufficient expansion in girth to displace belt segment 14 (FIG. 2) and close switch 22, alarm 26 will be triggered if the electrical current of the complete circuit travels through the delay circuit 28 for the predetermined period of time. The circuit is completed to allow current to flow from contact 40, through contacts A and B, to lead 44.

When the three-position switch 24 is switched by the user to the second ON position, contact C is connected to contact D, and contact E is connected to contact F as shown by broken lines 52,54. Thus, in the second ON position, the negative lead 46 from the battery 20 is connected to the negative contact 42 of the alarm 26 through contacts F and E, bypassing delay circuit 28. Therefore, when the momentary switch 22 is closed by a displacement of belt segment 14 resulting from a sufficient expansion in girth (or by other set-up means as described below), alarm 26 will be substantially immediately triggered.

Consequently, the girth monitoring belt 10 operates as follows. The subject places the belt 10 around the circumference of his or her mid-section, with the sensor housing 18 positioned over the umbilicus. The free end of the calibrated belt segment 14 is placed into the buckle 16 and the belt 10 tightened. The inches indicator to which the belt strap should be adjusted will vary from individual to individual, and initial testing is necessary to find an appropriate "starting point."

To find the correct "starting point", the subject slides the switch lever 33 to place the three-position switch 24 in the second ON (SET-UP/TEST MODE) position. This is the mode which bypasses the delay circuit 28 and will trigger the alarm 26 immediately upon switch 22 closing. The subject can now use one of several methods to establish the "starting point". In a first method, the user places two fingers between the abdomen and webbing to simulate an increase in girth. The buckle 16 is adjusted to decrease the circumference of the belt 10 until the tightening just activates the alarm 26. In a second method, the user pushes his abdomen outwardly to simulate the desired limit increase in girth, then adjusts the belt 10 to reduce the circumference of the belt until this circumference just activates the alarm. A third method involves consumption of a moderate volume meal, then adjusting the circumference of the belt 10 and buckle until the alarm is activated.

An inch and fractional inch reading can now be noted and recorded by referring to the calibration 15 closest to the end of the belt buckle 16. Once the setup steps, above, have been performed, the belt 10 is now ready to be used. The switch lever 33 of the three-position switch 24 is displaced to the first ON position (ON MODE). When the device 10 is correctly worn in this mode, the alarm 26 will activate after consumption of food volume sufficient to increase girth beyond what the set-up allows. This "start point" setting is preferably used by the subject each day, limiting the volume of food eaten at meals until waist size is decreased. As the waist size decreases, the subject should change the "start point" by adjusting the belt 10 to decrease the circumference further, if additional weight loss is desired.

It is preferable that the subject wear the belt 10 throughout the day, and only activate the belt prior to meals by placing the three-position switch 24 in the first ON position. In this mode, when the alarm 26 is triggered, it signals the subject that a desired volume of food has been consumed, and that the subject should cease further food intake. It should be noted that food intake can remain in the stomach from 30 minutes to 4 hours, so the consumption of food can be cumulative if the patient eats again soon after a meal. The present invention will therefore also respond to this cumulative factor.

In addition to using the present invention to limit and control food intake, the present invention can be used for the treatment of anorexia nervosa, a disorder related to self starvation in which the subject believes that he or she is much more overweight than he or she actually is and therefore refuses to eat. The device 10 can be used to treat this disorder in a reverse sense, i.e. for intentional weight gain. The subject, under a physician's care, wear's the belt 10 in the ON MODE and is instructed to eat until the alarm 26 is triggered. The physician can then progressively increase the inch and fractional inch settings 15 of the belt segment 14 until the desired girth and body weight have been achieved.

Having described in the invention in detail and by reference to the drawings, it will be apparent that modification and variations are possible without departing from the scope of the invention as defined in the following claims.

What is claimed is:

1. A device for monitoring a volume of food consumed by an individual comprising:
   a belt member shaped to fit about a waist of a user;
   a sensor including a sensor housing, an alarm, and an activation switch;
   said switch being operatively connected to said alarm such that activation of said switch, activates said alarm;
   said belt member being operatively connected to said sensor such that a tensile force applied to said belt member greater than approximately 15 ounces activates said switch;
   whereby when said belt member is worn about the waist of said user, a desired limit of increase in girth of said user at said waist, caused by a consumption of food by said user, applies a tensile force greater than approximately 15 ounces to said belt member, activating said switch, and in turn, activating said alarm.

2. The device of claim 1 wherein said sensor includes a delay circuit connected between said switch and said alarm such that said switch must be activated continuously for a desired time interval before said alarm is activated.

3. The device of claim 2 wherein:
   said belt member is connected at one end to said sensor housing and at another end to a sliding component, slidingly mounted to said sensor housing, thereby forming a closed loop shaped to fit about the waist of a user;
   said sliding component being operatively connected to said switch such that in one position of said sliding component with respect to said sensor housing said switch is activated, and in another position of said sliding component with respect to said sensor housing said switch is deactivated.

4. The device of claim 3 wherein said sensor housing is shaped to be worn about the waist of a user.

5. The device of claim 4 wherein said sensor includes a multiple position switch connected between said delay circuit and said alarm, said multiple position switch having a first position which connects said delay circuit to said alarm and a second position which bypasses said delay circuit such that activating said switch immediately activates said alarm.

6. The device of claim 5 wherein said sensor further comprises a power supply connected to said switch and said multiple position switch such that activating said switch allows said power supply to activate said alarm.

7. The device of claim 6 wherein said sensor includes a spring connected between said sliding component and said sensor housing and oriented to urge said sliding component to contact said switch such that a tensile force greater than approximately 15 ounces overcomes a compressive force of said spring and allows said sliding component to separate from said switch and thereby activates said switch.

8. The device of claim 7 wherein said belt member is adjustable in length to vary a circumference of said loop.

9. The device of claim 8 wherein said belt member includes first and second belt segments connected to said sliding component and said sensor housing, respectively, and a buckle connecting free ends of said first and second belt segments, said buckle providing adjustability of a length of said belt member.

10. A method of effecting weight loss by limiting the volume of food consumed at a meal comprising the steps of:
    attaching a belt about a torso of a user, said belt having a belt member shaped to fit about a torso of a user, and a sensor having an activation switch operatively connected to said belt member such that a tensile force applied to said belt member and sensor closes said activation switch, and an alarm connected to said switch to be activated by said closing of said switch, such that when said belt member is worn about the waist of said user, a desired limit of increase in girth of said user at said waist applies sufficient tensile force between said belt and said sensor to close said activation switch and activate said alarm;
    adjusting an effective circumference of said belt such that said alarm is activated by said desired limit of increase in girth of said user; and
    consuming food until said girth of said user increases sufficiently to exert tensile force on said belt sufficient to close said activation switch and activate said alarm.

11. The method of claim 10 wherein said consuming step includes the step of providing a time delay prior to said activation of said alarm of sufficient duration such that said alarm is not triggered by breathing of said user.

12. A device for monitoring a volume of food consumed by an individual, comprising:
    a sensor housing;
    a first belt segment having a device end and a free end, said device end being attached to said housing;
    a second belt segment having a device end and a free end, said device end being slidably attached to said housing;

a coupling for joining said free ends of said first and second belt segments;

a sensor for detecting a displacement of said second belt segment in a direction, relative to said housing, away from said first belt segment, said sensor emitting a signal in response to said detection;

a biasing element, coupled between said device end of said second belt segment and said housing, and having a predefined compression strength, wherein a tensile force greater than approximately 15 ounces must be applied to said second belt segment to cause said displacement;

an alarm triggered by said signal; and a power source connected to provide power to said sensor and said alarm.

13. The device of claim 12 wherein said biasing element is a spring having one end attached to said device end of said second belt segment and the other end attached to said housing, such that said spring resists said displacement of said device end of said second belt segment in said direction away from said first belt segment.

14. The device of claim 13 further comprising a delay circuit, connected between said sensor and said alarm and configured to trigger said alarm upon said sensor signal remaining at a predetermined state for a predetermined time.

15. The device of claim 14 further comprising a first switch for bypassing said delay circuit such that when said first switch is activated, said alarm will be triggered substantially immediately upon said sensor signal reaching said predetermined state.

16. The device of claim 15 further comprising a second switch for controlling said power source.

17. The device of claim 16 wherein said sensor emits said signal at said predetermined state when said device end of said second belt segment slides a predetermined distance in said direction away from said first belt segment.

18. The device of claim 12, wherein said coupling is an adjustable buckle.

19. A device for monitoring a volume of food consumed by an individual, comprising:

a sensor housing;

a first belt segment having a device end and a free end, said device end being attached to said housing;

a second belt segment having a device end and a free end, said device end being slidably attached to said housing;

a coupling for joining said free ends of said first and second belt segments;

a sensor for detecting displacement of said second belt segment in a direction, relative to said housing, away from said first belt segment, said sensor emitting a signal in response to said detection;

an alarm triggered by said signal;

a power source connected to said sensor and said alarm, to provide power to said sensor and said alarm;

a cradle attached to said housing;

a pin attached to said device end of said second belt segment, slidably carried in said cradle;

a spring having one end attached to said pin and the other end attached to said housing;

said sensor being a switch having a contact extending into said cradle such that said spring holds said pin in slidable contact with said switch contact until a force, sufficient to displace said device end of said second belt segment in said direction away from said first belt segment, is applied to said second belt segment.

20. A device for monitoring a volume of food consumed by an individual, comprising:

a sensor housing;

a first belt segment having a device end and a free end, said device end being attached to said housing;

a second belt segment having a device end and a free end, said device end being slidably attached to said housing;

a coupling for joining said free ends of said first and second belt segments;

a sensor for detecting displacement of said second belt segment relative to said housing, said sensor emitting a signal in response to said detection;

an alarm triggered by said signal;

a power source connected to said sensor and said alarm, to provide power to said sensor and said alarm;

a spring having one end attached to said device end of said second belt segment and the other end attached to said housing, such that said spring resists displacement of said device end of said second belt segment in a direction away from said housing;

a delay circuit, connected between said sensor and said alarm and configured to trigger said alarm upon said sensor signal remaining at a predetermined state for a predetermined time;

a first switch for bypassing said delay circuit such that when said first switch is activated, said alarm will be triggered substantially immediately upon said sensor signal reaching said predetermined state; and a second switch for controlling said power source;

said sensor emitting said signal at said predetermined state when said device end of said second belt segment slides a predetermined distance in said direction away from said housing; and said sensor includes a third switch, said third switch being oriented to be open by contact with said device end of said second belt segment and closed when not in contact with said device end of said second belt segment, said device end of said second belt segment separating from said third switch upon said device end of said second belt segment displacing said predetermined distance in said direction away from said housing.

21. A method of effecting weight loss by limiting the volume of food consumed at a meal comprising the steps of:

attaching a belt about a torso of a user, said belt including, a belt member shaped to fit about a torso of a user, a sensor operatively connected to said belt member such that a predetermined expansive tensile force applied to said belt member activates said sensor, and an alarm operatively connected to said sensor and activated by said activation of said sensor, such that when said belt member is worn about the waist of said user, a desired limit of increase in girth of said user at said waist causes said predetermined expansive tensile force to be applied to said belt, activating said sensor, and in turn activating said alarm;

adjusting an effective circumference of said belt such that said alarm is activated by said desired limit of increase in girth of said user; and consuming food until said girth of said user increases sufficiently to exert said predetermined expansive tensile force on said belt.

22. The method of claim 21, wherein said consuming step includes the step of providing a time delay prior to said activation of said alarm of sufficient duration such that said alarm is not triggered by breathing of said user.

23. The method of claim 21, wherein said predetermined expansive tensile force ranges from approximately 15 ounces to approximately 25 ounces.

* * * * *